United States Patent
Stone et al.

(10) Patent No.: US 7,819,881 B2
(45) Date of Patent: Oct. 26, 2010

(54) SEGMENTED JOINT DISTRACTOR

(75) Inventors: Kevin T Stone, Winona Lake, IN (US); Ryan C Lakin, Warsaw, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 871 days.

(21) Appl. No.: 11/502,498

(22) Filed: Aug. 10, 2006

(65) Prior Publication Data
US 2006/0293685 A1    Dec. 28, 2006

Related U.S. Application Data

(62) Division of application No. 10/614,657, filed on Jul. 7, 2003, now abandoned, which is a division of application No. 09/838,456, filed on Apr. 19, 2001, now Pat. No. 6,616,673.

(51) Int. Cl.
*A61B 17/60* (2006.01)
*A61F 2/00* (2006.01)

(52) U.S. Cl. ...................................... 606/105
(58) Field of Classification Search ............... 606/86 R, 606/90, 105; 623/22.12
See application file for complete search history.

(56) References Cited

U.S. PATENT DOCUMENTS

| | | | |
|---|---|---|---|
| 3,542,015 | A | 11/1970 | Steinman |
| 4,299,227 | A | 11/1981 | Lincoff |
| 4,312,353 | A | 1/1982 | Shahbabian |
| 4,727,744 | A | 3/1988 | Ferree |
| 5,019,042 | A | 5/1991 | Sahota |
| 5,059,194 | A * | 10/1991 | Michelson ............... 606/90 |
| 5,163,949 | A | 11/1992 | Bonutti |
| 5,176,683 | A | 1/1993 | Kimsey et al. |
| 5,213,112 | A * | 5/1993 | Niwa et al. ............. 600/587 |
| 5,308,327 | A | 5/1994 | Heaven et al. |
| 5,309,896 | A | 5/1994 | Moll et al. |
| 5,331,975 | A | 7/1994 | Bonutti |
| 5,468,244 | A * | 11/1995 | Attfield et al. ............ 606/90 |
| 5,601,556 | A * | 2/1997 | Pisharodi ............... 606/86 A |
| 5,620,457 | A | 4/1997 | Pinchasik et al. |
| 5,624,381 | A | 4/1997 | Kieturakis |
| 5,656,013 | A | 8/1997 | Yoon |
| 5,685,190 | A | 11/1997 | Yamamoto et al. |
| 5,743,852 | A | 4/1998 | Johnson |
| 5,782,740 | A | 7/1998 | Schneiderman |
| 5,820,595 | A | 10/1998 | Parodi |
| 5,910,101 | A | 6/1999 | Andrews et al. |
| 5,972,015 | A | 10/1999 | Scribner et al. |
| 5,984,943 | A | 11/1999 | Young |
| 6,015,421 | A | 1/2000 | Echeverry et al. |
| 6,017,305 | A | 1/2000 | Bonutti |
| 6,017,489 | A | 1/2000 | Woolf et al. |
| 6,048,346 | A | 4/2000 | Reiley et al. |
| 6,168,601 | B1 * | 1/2001 | Martini .................. 606/90 |
| 6,235,043 | B1 | 5/2001 | Reiley et al. |

* cited by examiner

*Primary Examiner*—Anu Ramana
(74) *Attorney, Agent, or Firm*—Harness, Dickey

(57) ABSTRACT

A method of separating two articulating surfaces of a joint is provided. The method includes providing a distractor having a series of generally spheroidal members. The method also includes inserting the distractor into the joint, and moving the distractor to separate the two articulating surfaces.

20 Claims, 4 Drawing Sheets

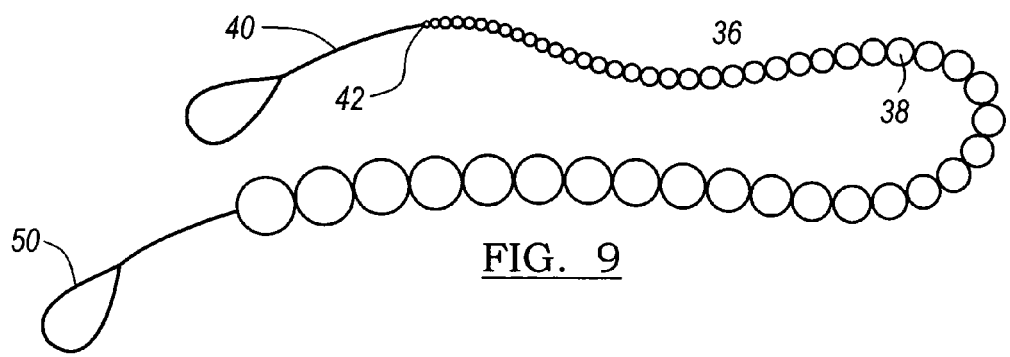
FIG. 9
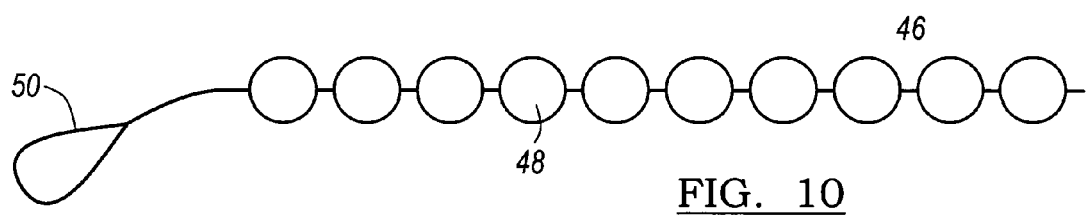
FIG. 10
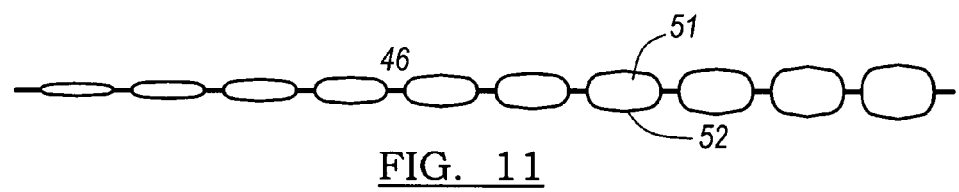
FIG. 11
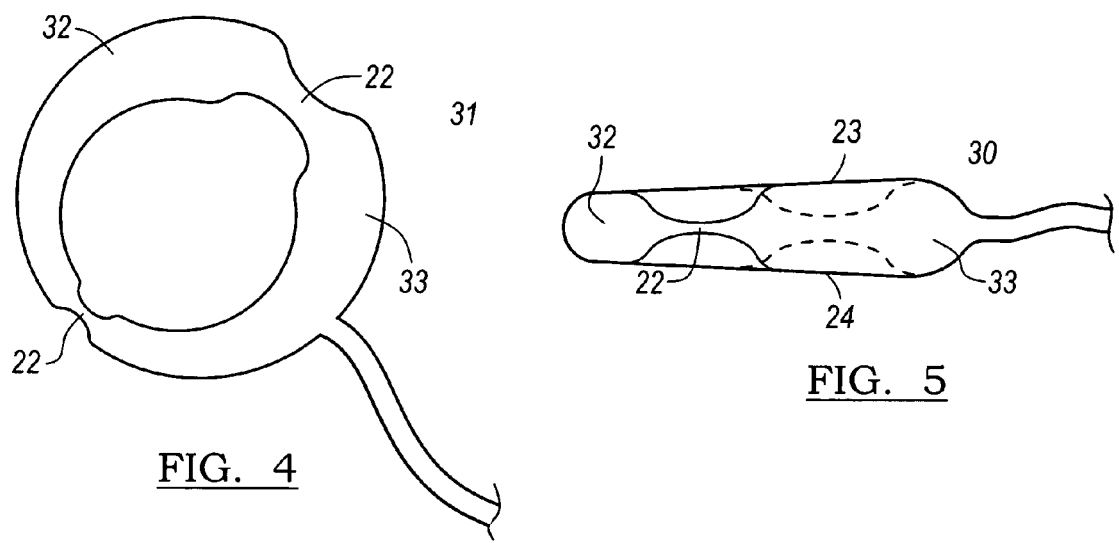
FIG. 4
FIG. 5

SEGMENTED JOINT DISTRACTOR

CROSS-REFERENCE TO RELATED APPLICATIONS

This application is a divisional of U.S. patent application Ser. No. 10/614,657, filed on Jul. 7, 2003, which is a divisional of U.S. patent application Ser. No. 09/838,456, filed on Apr. 19, 2001 which issued on Sep. 9, 2003 as U.S. Pat. No. 6,616,673. The disclosures of the above referenced applications are incorporated herein by reference. The disclosures of the above referenced applications are incorporated herein by reference.

BACKGROUND

The present disclosure generally relates to an orthopedic instrument used to distract a joint, and more particularly, to a segmented joint distractor which allows for access into a distracted joint.

Joint arthroscopy is a relatively young treatment modality for treating painful joints. Its primary function is to diagnose joint pathology. Additionally, debridement, joint flushing and smoothing of the joint surfaces has led to reduced pain and a return to more normal activities.

An important step in arthroscopy is to assure that not only are the bones of the joint properly aligned, but also that both joint surfaces are accessible. Failure of both joint surfaces being accessible can lead to significant trauma to the surrounding joint soft tissue, which leads to significant recovery time.

The joint surfaces are spanned by muscles, ligaments or other soft tissue. For example, in the knee joint, the collateral ligaments are both equally tight in the joint. This tension in the collateral ligaments prevents sideways toggle of the appendage. The ACL and PCL limit the amount of anterior and posterior motion in the knee joint. These ligaments limit the amount the joint can be separated to create access to the joint surfaces.

The knee is a superficial joint because there is little soft tissue between the skin and the joint as compared to the hip. Access is achieved by a combination of flexion and extension to give the clinician direct view of the various anatomic structures. At times, hand distraction and rotation can be used to increase exposure.

While the current disclosure has more application in total joint surgery where ligament balancing is key, it has uses in other surgical procedures. In another example, gaining access to the bearing surfaces of a hip joint with minimal tissue disruption is often complex and relatively ineffective. Current methods, for example, to perform hip arthroscopy utilize elongated arthroscopy instruments to obtain access to the joint which lies under many thick layers of muscle and soft tissue. Distraction normally is applied to the leg to create approximately 5 to 7 millimeters of joint displacement. Access to limited portions of the intra-articular area can then be achieved.

This distraction of the joint applies force to the patient's foot and a counterforce to the patient's groin area. This mode of distraction is only marginally effective. Possible side effects to this surgery include numbness, nerve damage, and impotence. Additionally, the immobilized leg is not free to be manipulated to allow visualization of the articular cartilage areas.

Other apparatus attempt to separate various inner body regions by use of a fluid operated regulator. Typically, a balloon is positioned at the desired location within the body for developing an atomic space at the desired location. The apparatus typically includes a tunneling member and an inflatable balloon. The tunneling member has a substantially rigid tubular shaft with proximal and distal ends and a passage extending through the ends, and having an opening in the proximal end to receive an inflatable balloon. The balloon generally comprises a substantially flexible, and preferably non-elastic, material having an inflatable space therein, defining a predetermined shape capable of assuming collapsed and inflated conditions.

Inherent with these types of balloon distractors, is that the surface which needs to be observed or worked on is often covered by the balloon material. Inherent in arthroscopic surgeries is a need to access joint surfaces. As such, what is needed then is a joint distractor that does not suffer from the above-mentioned disadvantages. This, in turn, will provide a substantially conforming joint distractor between the articular cartilage areas, allow for visualization of the articular cartilage areas, and allow for debridement, joint flushing, and smoothing of the joint surfaces.

SUMMARY

In accordance with the teachings of the present disclosure, a method of separating two articulating surfaces of a joint is provided. The method includes providing a distractor having a series of members. The method also includes inserting the distractor into the joint, and moving the distractor to separate the two articulating surfaces.

In one of various embodiments, a method of separating two articulating surfaces of a joint is provided. The method includes providing a distractor having a series of members. The method also includes inserting the distractor into the joint. The method further includes pulling the distractor through the joint to separate the two articulating surfaces.

The present disclosure further provides a method of separating two articulating surfaces of a joint. The method includes providing first handle operably interconnected to a series of members, and coupling the series of members together. The method also includes passing the first handle into the joint. The method includes moving the first handle to separate the two articulating surfaces, and inserting at least one instrument into a space defined by the members.

DRAWINGS

Still other advantages of the present disclosure will become apparent to those skilled in the art after reading the following specification and by reference to the drawings in which:

FIG. 1 discloses a top view of the compartmentalized joint distractor according to the teachings of an embodiment of the present disclosure;

FIG. 4 is a view of an alternative embodiment of the present disclosure;

FIG. 5 is a side view of the alternative embodiment of FIG. 4;

FIG. 9 is a view of a fifth alternative embodiment of the present disclosure;

FIG. 10 is a view of a sixth alternative embodiment of the present disclosure;

FIG. 11 is a side view of the embodiment shown in FIG. 10; and

DETAILED DESCRIPTION

The following description of the various embodiments concerning a joint distraction apparatus are merely exemplary in nature and not intended to limit the present disclosure, its application, or uses. Moreover, while the present disclosure is described in detail with respect to a hip joint, it will be appreciated by those skilled in the art that the present disclosure is clearly not limited to use in distracting a hip joint and may be applied to various other types of joints or body structures, as further discussed herein.

Figure 1:
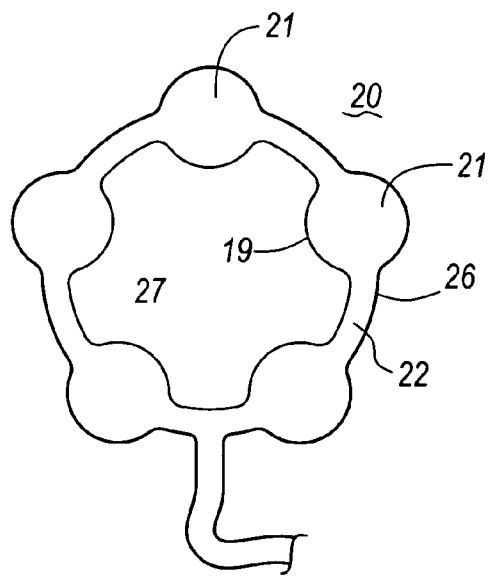
Figure 2:
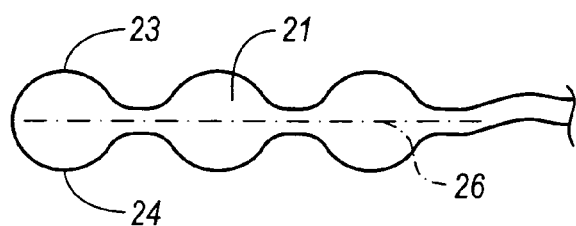
FIG. 2 is a side view of the compartmentalized joint distractor as shown in FIG. 1.

Referring to FIGS. 1 and 2, there is shown a joint distractor 20 according to the teachings of the various embodiments. The joint distractor 20 is composed of a pair of generally planar non-elastic polymer members 23 and 24. These polymer members 23 and 24 are coupled together along the inside 19 and outside edges 26 to form a hollow toroid. Formed on the toroid is the series of hollow fluidly coupled generally spheroid members 21. Each of the fluid containing bodies 21 is joined by the tube regions 22. Prior to inflation, the distractor 20 is flat and the planar members 23 and 24 lie in contact with each other.

The fluid in the fluid containing bodies 21 functions to apply pressure to the generally planar elastic or non-elastic members 23 and 24. The members 23 and 24 then in turn apply forces to the articulating surfaces 25 of the joint to separate them. This force is in direct opposition to the forces generated by the ligaments of the joint.

The inside edge 19 of the distractor defines a generally circular area 27 that generates the exposed joint surface 25. These exposed surfaces can then be accessed by the many orthopedic instruments which can enter the generally circular area 27 by passing adjacent the tube regions 22.

Figure 3:
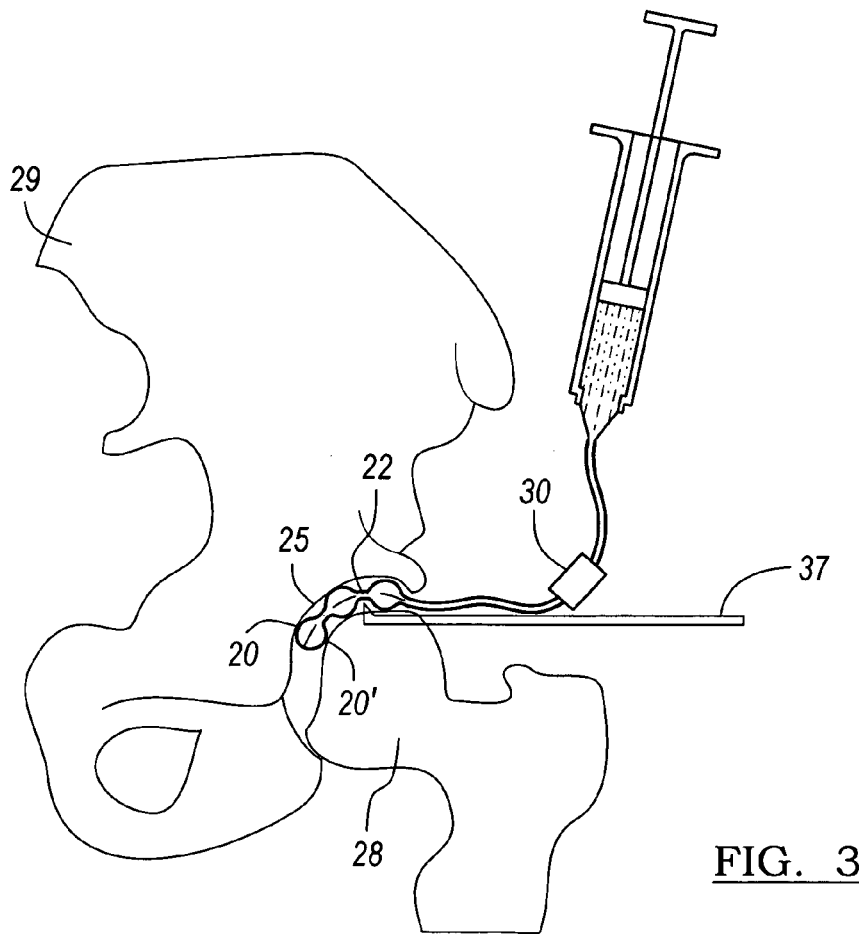
FIG. 3 is a view of the compartmentalized joint distractor of FIGS. 1 and 2 shown disposed within a hip joint.

As shown in FIG. 3, uninflated distractor 20' is positioned adjacent to the surfaces to be separated by insertion through a small incision. The femoral component 28 of the hip joint is partially distracted from the pelvis 29 only enough to position the uninflated distractor 20' between the joint surfaces 25. After insertion between the joint surfaces 25, sterile fluid is injected under pressure by a pressurized fluid source such as a syringe into the sealed distractor 20, filling the generally spheroid members 21.

Once the pressurized fluid fills the generally spheroid members 21, access to the articular cartilage surfaces 25 of the joint is available in the circular region 27, by passing the orthopedic instruments between the inflated spheroids 21 via an appropriate incision. As best seen in FIG. 3, orthopedic instruments 37 can access the articular surface 25 adjacent to the tube region 22. Each fluid distractor 20 preferably includes a valve 30 that regulates the fluid in and out of the spheroids 21. The valve 30 functions to allow fluid into the distractor 20 while it is being pressurized. The sterile fluid can be removed from the distractor 20 by puncturing the surface 23 of the distractor or by releasing fluid through the valve 30.

FIGS. 4 and 5 represent views of an alternative embodiment of the present disclosure. Shown is the toroidal joint distractor 31 which is formed by a pair of generally crescent shaped fluid filled spheroids 32 and 33. Coupling the crescent shaped spheroids 32 and 33 are a pair of adjoining fluidly filled tube regions 22. Although the toroidal distractor 31 has fewer tube regions 22 to insert orthopedic instruments 37, the crescent shaped spheroids 32 and 33 provide a larger surface area which impart force on the articular surface 25. The polymer members 23 and 24 forming the crescent shaped spheroids 27 and 28 can be coupled so as to form an angled wedge structure should a particular use call for one.

Figure 6:
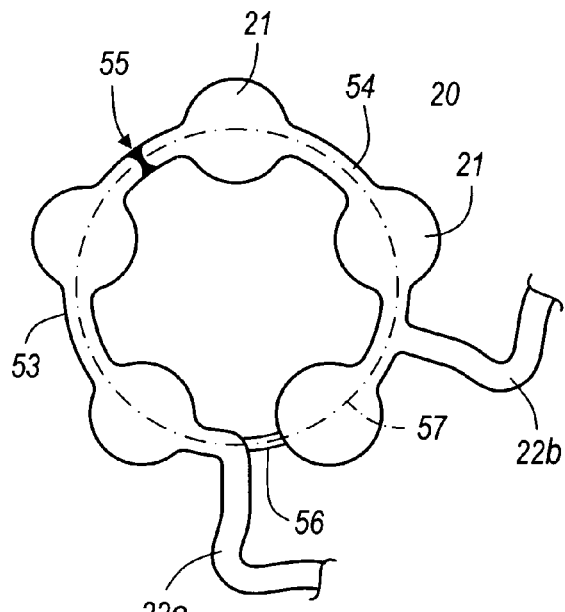
FIG. 6 is a view of a second alternative embodiment of the present disclosure.

With reference to FIG. 6, there is shown a joint distractor 20 according to the teachings of a second alternative embodiment of the present disclosure. The joint distractor 20 is composed of two fluidly isolated chambers 53 and 54. These chambers 53 and 54 are each formed by at least one generally spheroid member 21. Each of the chambers 53 and 54 are capable of being filled by separate fluid sources through the tube regions 22a and 22b. Additionally, the separate regions are non-fluidly coupled at regions 55 and 56. As is depicted in FIG. 6, any of the distractors of the present disclosure can have radio opaque materials 57 such as the wire shown in FIG. 6. These radio opaque materials 57 can take the form of particulate incorporated within the distractor devices 20. When placed within a joint the joint distractor as depicted in FIG. 6 can be used to vary the angle of the joint by increasing or decreasing the amount of fluids in the chambers 53 and 54. By modifying the amount of fluid within the chamber, access to the joint can be obtained adjacent to tube regions 22.

Figure 7:
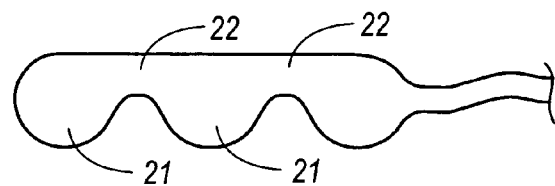
FIG. 7 is a view of a third alternative embodiment of the present disclosure.
Figure 8:
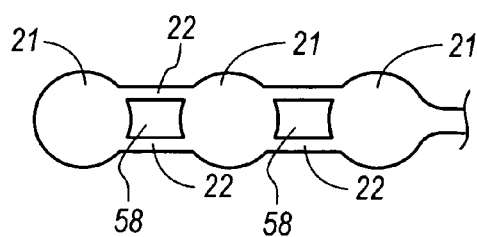
FIG. 8 is a view of a fourth alternative embodiment of the present disclosure.

FIGS. 7 and 8 show side views of the third and fourth alternative embodiments of the present disclosure. Shown in FIG. 7 is the connected tube region 22 disposed on the top surface of the distractor. This allows for access of the joint area under the tube region 22 and the spaces defined. FIG. 8 shows a plurality of generally spheroidal members 21 coupled by tube members 22 located on the top and bottom surface of the joint distractor. The tube members define openings 58 between the tube members and the generally spheroidal bodies 21. Access to the joint surfaces by medical instruments can be obtained adjacent the tube regions 22.

Figure 12:
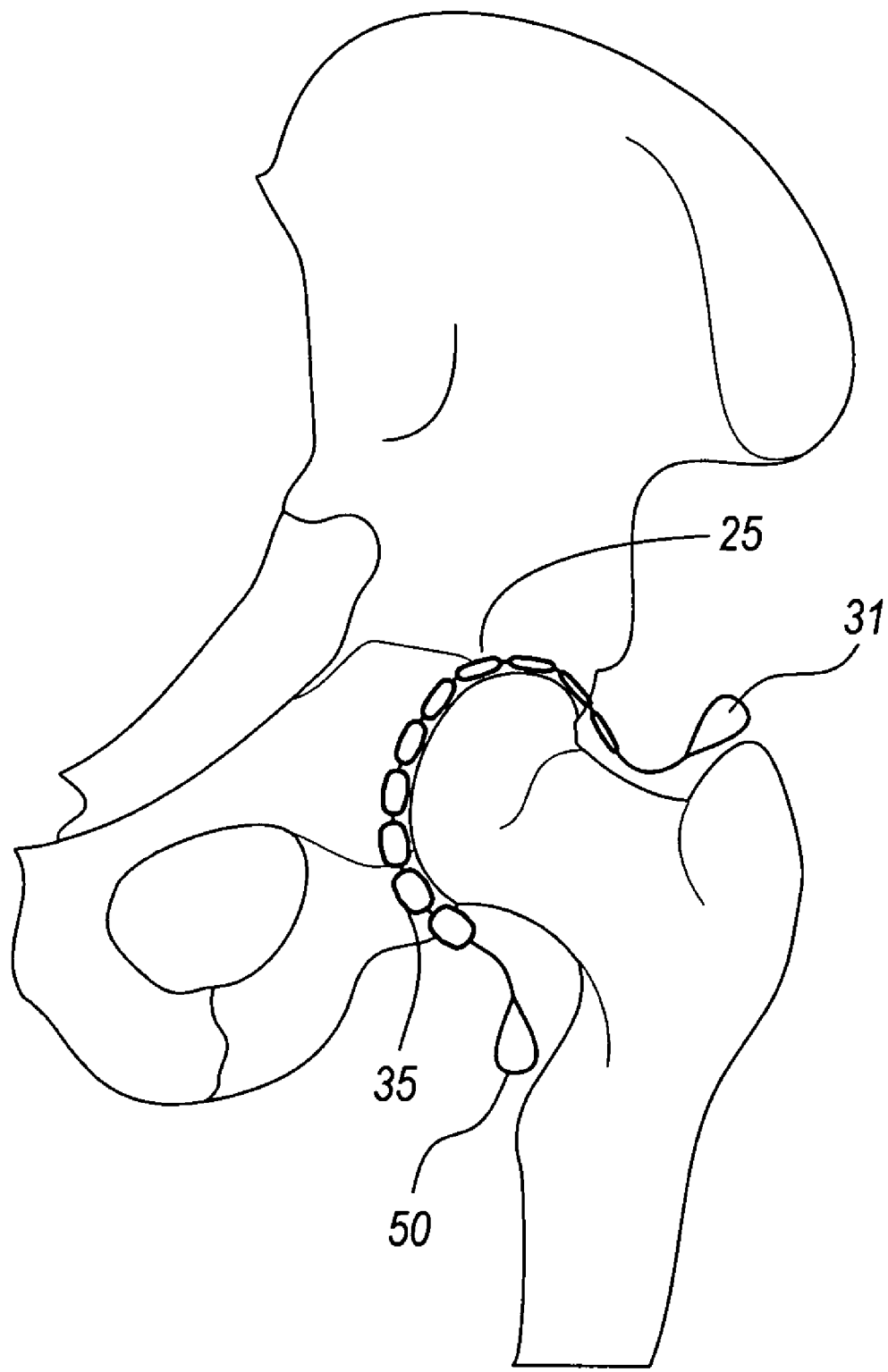
FIG. 12 is a view of the compartmentalized joint distractor of FIG. 10 distracting a joint.

With reference to FIG. 9, a fifth alternative embodiment of the present disclosure is shown. Shown is a distractor 36 having a series of generally spherical elements 38 on a cord 40 having handle elements 50. The string of spherical elements 36, which is pulled through a joint region, functions to separate and hold the joint articular cartilage surfaces 25 apart. The joint is first distracted slightly to separate the surfaces enough to allow passage of the distractor's cord 40. The cord 40 is then pulled through the region from smallest diameter spherical element 42 to a point along the distractor that there is sufficient access space created (see FIG. 12). Access to the joint can be obtained by the use of instruments placed in regions between the spherical elements 38. The spherical elements 38 can be used to hold the surfaces apart after the joint has been distracted by applying forces to separate the members. It is envisioned that the spherical elements 38 be solid or fluid filled.

The series of adjacent spheres 38 are mounted onto a cord or articulating member 40, which is made of fibers or wire by being integrally molded thereon. The spherical elements 38 have an increasing diameter from about 2 mm to about 10 mm, each spherical element 38 increasing in size by about 0.2 mm. The spherical elements 38 can be adjacent one another or can be spaced apart, leaving room between for access by orthopedic instruments 37.

In another embodiment of the present disclosure, shown in FIG. 10 is a top view of a segmented distractor 46 according to the teachings of a sixth alternative embodiment of the present disclosure. As can be seen, the distractor 46 has a series of generally circular distractor components 48, each having the same diameter. Also shown are the handle members 50 which are used to pull the through the joint. FIG. 11 shows a side view of the distractor 46 as shown in FIG. 10. As can be seen, the circular distractor components 48 have varying thicknesses. The thickness of the distractor components 48 increases from about 2 mm to about 10 mm. Each of these segments has a pair of generally parallel planar regions 51 and 52 with each adjoining distractor component 48 defining a slightly larger thickness. The planar regions optionally can have a slightly angled surface to assist in the facilitation of the separation of the joint.

A wide variety of features can be utilized in the various material disclosed and described above. The foregoing discussion discloses and describes the various embodiments of the present disclosure. One skilled in the art will readily recognize from such discussion, and from the accompanying drawings that various changes, modifications, and variations can be made therein without departing from the true spirit and fair scope of the present disclosure.

What is claimed is:

1. A method of separating two articulating surfaces of a joint of a hip having a femoral head and an acetabulum in part with a distractor comprising:
   distracting externally the femoral head from the acetabulum a first space;
   inserting the distractor in the first space between the femoral head and the acetabulum;
   contacting the femoral head and the acetabulum with a fixed size member of the distractor;
   moving the distractor in the first space to sequentially contact the femoral head and the acetabulum with a plurality of fixed size members having a serially increasing fixed size;
   distracting internally the femoral head from the acetabulum to create a second dimension in the first space;
   performing a medical procedure in the first space;
   decreasing the internally distracted dimension between the femoral head and the acetabulum; and
   removing the distractor from the joint.

2. The method of claim 1, further comprising:
   passing at least one instrument into the first space defined between the members; and
   performing a procedure on at least one of the articulating surfaces.

3. The method of claim 1, further comprising:
   providing a cord coupled to the plurality of the fixed size members having an increasing dimension among the plurality of the fixed size members; and
   providing a first handle coupled to a first end of the chord;
   wherein the fixed size members are solid.

4. The method of claim 3, wherein the plurality of the fixed size members are provided as a series of members with an increasing dimension;
   arranging the series of the fixed size members on the cord such that a first fixed size member with a small dimension is adjacent to the first handle, and the dimension of each of the following fixed size members in the series of the fixed size members gradually increases in a direction away from the first handle; and
   wherein moving the distractor includes moving the cord to move the series of the fixed size members to gradually increase the second dimension between the femoral head and the acetabulum.

5. The method of claim 3, further comprising:
   selecting the fixed size members to have a shape that is one of generally spheroidal, flattened on a side, planar, or elongated;
   wherein the selected fixed size member shape is unchanged during moving the distractor.

6. The method of claim 1, further comprising:
   viewing the first space via an arthroscope.

7. A method of separating two articulating surfaces of a joint comprising:
   providing a distractor having a series of rigid and fixed size members flexibly interconnected to one another;
   distracting the joint slightly a first amount;
   inserting the distractor into the joint that is slightly distracted; and
   pulling the distractor through the joint to separate the two articulating surfaces to a second amount greater than the first amount while maintaining at least partial contact of the joint.

8. The method of claim 7, further comprising:
   inserting at least one instrument through a region defined between the series of the rigid and fixed size members; and
   performing a procedure on at least one of the articulating surfaces.

9. The method of claim 7, further comprising:
   providing a first handle coupled to a first end of the distractor and a second handle coupled to a second end of the distractor;
   inserting the first handle into the joint; and
   pulling the first handle to separate the two articulating surfaces.

10. The method of claim 9, further comprising:
    providing the series of the rigid and fixed size members with an increasing dimension;
    arranging the series of members on the distractor such that a first rigid and fixed size member with a smallest of the dimension is adjacent to the first handle, and the dimension of each of the following rigid and fixed size members gradually increases in the dimension from the first handle to the second handle; and
    moving the distractor to move the series of the rigid and fixed size members between the two articulating surfaces in a sequential motion from smallest towards largest to enable a gradual increase in the separation distance between the two articulating surfaces.

11. The method of claim 7, wherein providing the series of the rigid and fixed size members further comprises:
    coupling together the rigid and fixed size members with an exterior surface that is flat or curved.

12. The method of claim 7, wherein distracting the joint slightly includes moving a femoral head a distance from an internal articulation surface of an acetabulum to create a first space; and wherein inserting the distractor includes moving the distractor into the first space to move the femoral head less than about 10 centimeters from the internal articulation surface of the acetabulum.

13. A method of separating two articulating surfaces of a joint defined by two boney portions, comprising:
    providing an instrument including:
       providing a first end with a first handle;
       providing a series of rigid members;
       coupling the series of rigid members together;
    passing the first handle into the joint;
    pulling the first handle to contact the boney portions with at least a portion of the series of rigid members to separate the two articulating surfaces;
    inserting at least one instrument into a space defined between the two articulating surfaces formed by pulling the first handle; and
    preparing at least one of the two articulating surfaces.

14. The method of claim 13, further comprising:
arranging the series of rigid members on the instrument such that a first of the series of rigid members with a small fixed dimension is adjacent to the first handle and the fixed dimension of each of the following members in the series of members increases in a direction away from the first handle; and
pulling the instrument moves the series of rigid members to gradually increase a separation distance between the two articulating surfaces.

15. The method of claim 13, wherein providing the series of rigid members further comprises:
providing the series of rigid members with an exterior surface that is flat or curved.

16. The method of claim 13, wherein providing the series of rigid members further comprises:
providing a series of bone contacting members.

17. The method of claim 13, wherein providing the series of rigid members further comprises:
selecting the rigid members to be one of generally spheroidal, flattened on a side, having a planar region or elongated.

18. The method of claim 13, wherein preparing at least one of the two articulating surfaces includes:
moving an instrument between the series of rigid members; and
obtaining access to the tissue in a hip joint.

19. The method of claim 18, wherein obtaining access to a hip joint includes:
maintaining mobility of a leg and not distracting the hip joint.

20. The method of claim 13, further comprising:
first preparing the joint by initially moving the two articulating surfaces a first distance apart while maintaining the mobility of the joint; and
moving the instrument into the prepared joint to allow for internal distraction of the joint;
wherein pulling the first handle causes distraction of the joint from an interior of the joint.

* * * * *